United States Patent [19]

Hofmann

[11] 4,018,579
[45] Apr. 19, 1977

[54] APPARATUS FOR PRODUCING DRY COMPRESSED AIR

[75] Inventor: Hans-Joachim Hofmann, Geradstetten, Germany

[73] Assignee: Durr - Dental KG, Germany

[22] Filed: Apr. 18, 1975

[21] Appl. No.: 569,450

[30] Foreign Application Priority Data

Apr. 20, 1974 Germany .................. 2419178
Apr. 10, 1975 Switzerland .................. 4548/75

[52] U.S. Cl. .................. 55/213; 55/218;
55/269; 55/272; 55/276; 55/283; 55/288;
55/316; 55/337; 55/DIG. 34; 236/44 A;
137/203

[51] Int. Cl.[2] .................. B01D 50/00

[58] Field of Search ............ 55/163, 185, 186, 195,
55/200, 210, 217, 218, 269, 270, 275, 316,
417, DIG. 17, DIG. 34, 337, 320, 213, 208,
268, 323, 272, 283, 288, 302, 485; 236/44 A;
34/50; 137/203, 204

[56] References Cited

UNITED STATES PATENTS

| | | | |
|---|---|---|---|
| 2,322,603 | 6/1943 | Thumim et al. | 55/163 |
| 2,669,321 | 2/1954 | Schmidlin | 55/218 |
| 2,950,728 | 8/1960 | Watrous | 137/82 |
| 2,955,673 | 10/1960 | Kennedy et al. | 55/163 |
| 2,988,102 | 6/1961 | Harry et al. | 55/218 X |
| 3,261,146 | 7/1966 | Malec | 55/218 |
| 3,417,547 | 12/1968 | Rapp | 55/269 X |
| 3,472,000 | 10/1969 | Glass et al. | 55/163 |
| 3,483,980 | 12/1969 | Cochran et al. | 55/269 X |
| 3,563,458 | 2/1971 | Martin | 236/44 A |
| 3,572,008 | 3/1971 | Hankison et al. | 55/186 X |
| 3,763,338 | 10/1973 | Tozer | 236/44 A |

Primary Examiner—Frank W. Lutter
Assistant Examiner—David L. Lacey
Attorney, Agent, or Firm—Robert E. Burns; Emmanuel J. Lobato; Bruce L. Adams

[57] ABSTRACT

Apparatus for producing dry compressed air comprises a compressor, a separator to remove condensates, an adsorption filter to filter and dry the air and a storage tank. A valve for controlling reverse flow of air from the storage tank through the filter to the atmosphere to regenerate the adsorption filter when the compressor stops is controlled by a moisture sensitive device so that reverse flow is permitted only if the moisture control of the compressed air is above a predetermined value. The opening of a tap to discharge collected liquid from the separator is controlled by a pneumatically operated valve system so that no electrical control is required.

20 Claims, 7 Drawing Figures

APPARATUS FOR PRODUCING DRY COMPRESSED AIR

FIELD OF INVENTION

The present invention relates to an apparatus for producing dry compressed air having a source of compressed air which supplies compressed air to a storage container through an absorption filter and having return devices for returning dry, compressed air through the adsorption filter for the regeneration of the latter with the source of compressed air disconnected.

BACKGROUND OF THE INVENTION

In the production of compressed air by drawing air from the atmosphere and compressing it, copressed air which is supersaturated in water vapor is obtained due to known physical relationships, thus leading to the formation of water of condensation which must be removed from the system. After the removal of the water of condensation, however, there still remains compressed air which is saturated with water vapor so that more water of condensation is again produced upon a slight decrease in the temperature. Furthermore in the ordinary plants for the production of compressed air such as is used in many companies it can generally not be avoided that some of the grease and oil used for lubricating the compressor will enter the compressed air or that the compressed air furthermore contains particles of dust and microorganisms which are drawn in by the compressor together with the atmospheric air. In many cases it is permissible for the compressed air to be relatively moist and dirty. This is true in particular in cases in which relatively robust compressed air units are to be driven or where the compressed air is used for the cleaning of machine parts, as for instance in automobile workshops. On the other hand, there are a number of uses in which compressed air which is not only dry but also free of dust and microorganisms is required. This is true in particular for the use of compressed air in the field of medicine, for instance for the driving of drills for dentists. The situation is similar in the case of sensitive pneumatic controls in which the formation of water of condensation and the occurrence of particles of dust would cause disturbances in operation. The presence of traces of oils and greases in the compressed air is also frequently not permissible since such residues may lead to disturbances in operation or, as for instance in dentistry, can lead to a taste or odor which is annoying to the patient.

In view of the frequent demand for dry compressed air which is very clean and—particularly in the field of medicine—also free of microorganisms, plants for the production of dry air have been developed in which very favorable results are obtained with respect to the quality of the dry compressed air by the combining of at least one adsorption filter with additional filter devices for the filtering out of solids and oil residues.

One such plant is described, for instance, in U.S. Pat. No. 3,399,510 where the compressed air supplied by a compressor after it had passed through an oil and water separator is fed to an adsorption filter in which further mechanical filtration as well as very intensive drying are effected. In the known dry air plant a compressed air storage tank as well as an auxiliary tank are fed from the output of the adsorption filter. The auxiliary tank serves to receive a predetermined quantity of compressed air which is returned into the atmosphere through the adsorption filter and a tap opening provided in the region of the oil and water separator immediately upon the stopping of the compressor as the result of a predetermined maximum pressure having been reached in the compressed air storage tank. The adsorption filter is regenerated by the dried air flowing from the auxiliary tank normally the same operating conditions are essentially present as were present at the start of the preceding operation cylce of the compressor. The known plant, however, fails when large quantities of compressed air are removed for a longer period of time from the compressed air tank since in this case the compressor operates for a very long time without a regeneration of the adsorption filter taking place. Furthermore the known plant is very unfavorable inasmuch as it is not capable of taking into account varying environmental conditions such as variations in the temperature and the humidity of the air, so that the amount of air in the auxiliary tank is too large for most cases but too small for some cases to bring about a sufficient regeneration of the adsorption filter, which on the one hand leads to an unfavorable efficiency and on the other hand to variations of the quality of the compressed air in the compressed air tank. Similar problems arise also in those plants which operate with two adsorption filters which are generally used alternately by means of a time control for filtration and drying and regenerating. Such a plant which has two adsorption filters is described, for instance, in German Pat. No. 1,282,608.

SUMMARY OF THE INVENTION

Starting form the problem indicated above and from the above indicated prior art, an object of the present invention is to maintain narrow tolerances for the moisture content of the compressed air with the same or improved quality of the compressed air under various environmental and operating conditions and to improve the efficiency of the apparatus.

This object is achieved by apparatus in accordance with the invention by the feature that the return devices comprise a valve which can be actuated as a function of the moisture of the compressed air in the compressed air tank. In this way the advantage is obtained that a regenerating cycle need be started only when there is actually a need for it in view of the amount of moisture already taken up by the adsorption filter. Unnecessary regenerating cycles are therefore avoided whereby the efficiency of the apparatus is improved.

In accordance with a further feature of the invention the dry air for the regenerating of the adsorption filter is taken, from the compressed air storage container from which the operating air is also taken. The further advantage is thereby obtained that one can dispense with an additional auxiliary tank. This leads to considerable savings in expense and with respect to the space required as well as with reference to the required conduit and valve means.

It has proven particularly favorable if the moisture sensitive valve is actuated by a feeler element the dimensions of which change as a function of the moisture so that the changes in shape of the feeler element can be utilized more or less directly for the opening and closing of the valve without the interposing of electromechanical converters or the like being necessary. In this connection, feeler elements in the shape of resin or plastic bands have been found to be very advantageous since the change in length of such a plastic band as a function of the moisture content of the compressed air in the compressed air storage container can be used in a very simple manner for the actuating of one of the valve elements, particularly if a suitable lever mechanism is employed.

As source of compressed air for the apparatus in accordance with the invention use may be either of a compressor or of a normal compressed air connection which is already available at the work site in question but which delivers compressed air of inadequate quality which must be additionally cleaned and dried in order that it can be used for the above mentioned special cases of use.

BRIEF DESCRIPTION OF DRAWINGS

The objects and advantages of the invention will be explained in further detail below with reference to the accompanying drawings in which.

DESCRIPTION OF PREFERRED EMBODIMENTS

Figure 1:
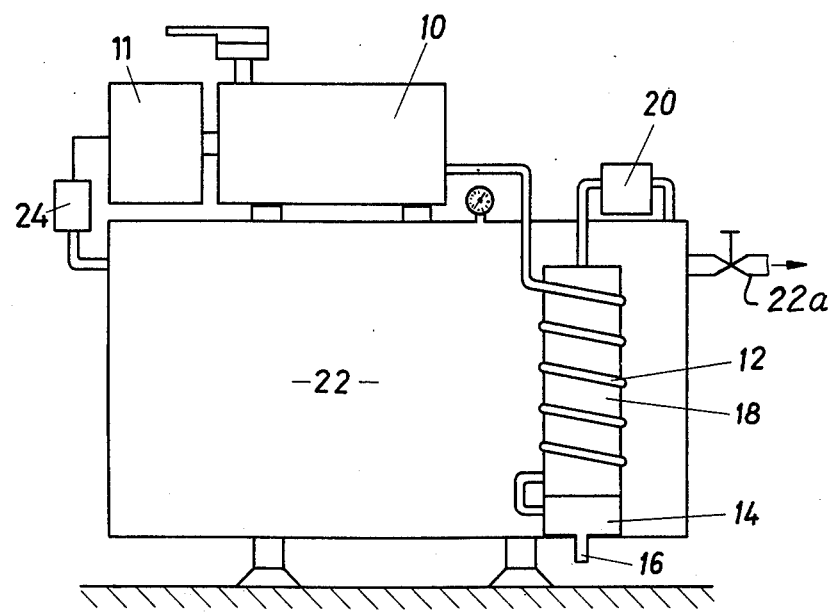
FIG. 1 is a diagrammatic showing of an apparatus including a separator and adsorption filter for the producing of dry compressed air.

The apparatus shown schematically in FIG. 1 comprises a compressor 10 with motor 11 as a source of compressed air, followed by a cooler 12. It is obvious that when an ordinary compressed air system serves as a source of pressure, the cooling device can be dispensed with. Downstream of the cooling device 12 there is a separator 34 which customarily includes an oil and water trap and which has a tap opening 16 for discharging collected liquid. The opening of the tap opening 16 is controlled by a valve system 14. Downstream of the separator 34 and valve system 14 there is a drier and filter 18 which, as can be seen from FIG. 2, comprises an adsorption filter 30 and additional mechanical or screening filters which are described below. The filter 18 is connected with a compressed air storage tank 22 through a second valve system 20. As long as the compressor 10 is in operation or as long as compressed air is supplied from a compressed air system, the unpurified compressed air, after cooling and after removal of liquid droplets by the separator 34, flows through the filter 18 where it is further purified and dried and through the second valve system 20 into the compressed air storage tank 22. During this operating phase, the apparatus of FIG. 1 operates in customary manner and, except as described below, essentially with the use of ordinary parts or groups of parts a detailed description of which can therefore be dispensed with here. As soon as a predetermined pressure has built up in the compressed air storage tank 22, the compressor 10 is disconnected by a pressure sensitive switch 24 which is in communication with the interior of the compressed air tank 22.

In a known device of the type described above which operates with a single adsorption filter, a regeneration cycle is introduced automatically upon the disconnecting of the compressor 10, during the course of which cycle a predetermined quantity of dry compressed air from an auxiliary storage tank is passed through the filter 18 and blown out into the atmosphere through the tap opening 16 of the separator 34. However, in the case of the apparatus shown in FIG. 1, the second valve system 20, as will be explained in further detail below, is so developed that a regeneration cycle is only introduced when the moisture of the compressed air in the compressed air tank 22 reaches or exceeds a predetermined upper limit. Furthermore, the compressed air required for regenerating the filter 18 is taken directly from the compressed air storage tank 22 and not from an auxiliary tank, as in the previously known devices.

Figure 2:
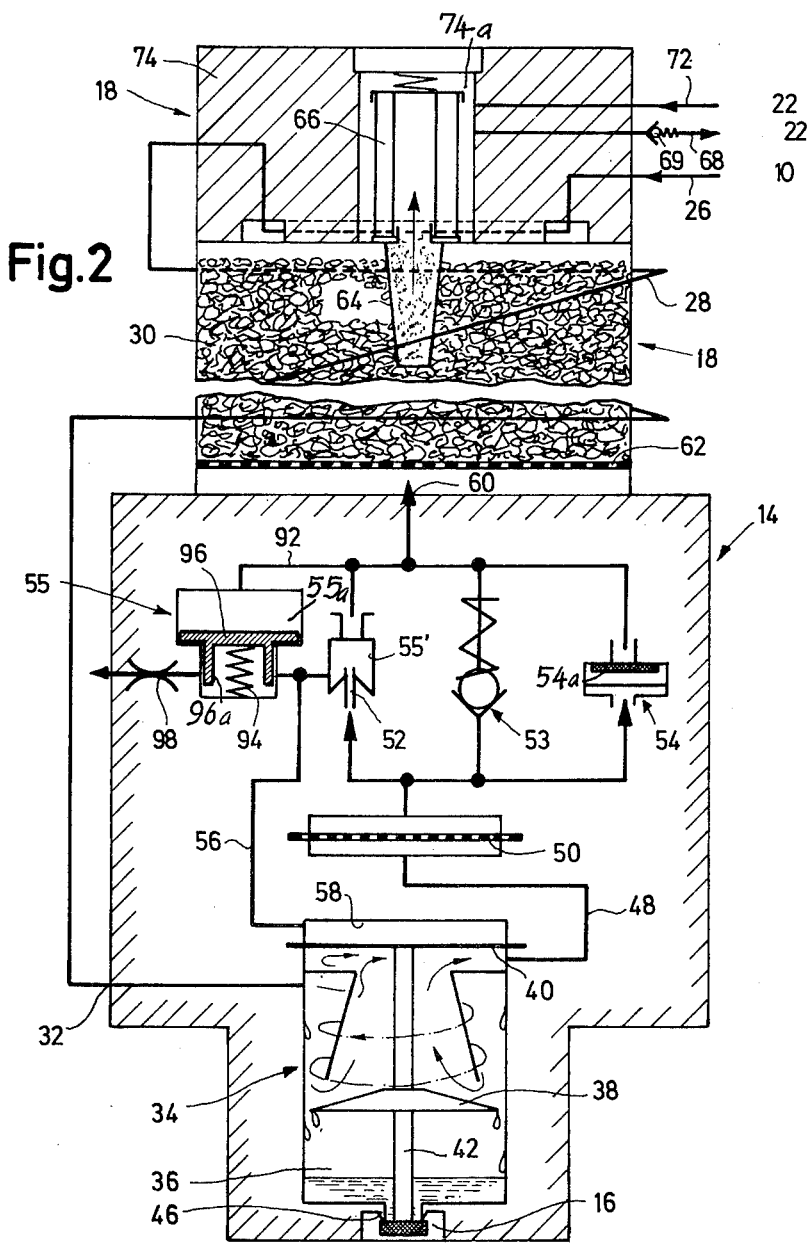
FIG. 2 is an enlarged schematic longitudinal section through the separator and adsorption filter of the apparatus of FIG. 1 and through an associated valve system.

In one preferred embodiment of an apparatus in accordance with FIG. 1, the filter 18 as well as the separator 34 and the valve system 14 are combined to form a structural unit which is shown in FIG. 2, which furthermore shows the cooling device 12 as well as a part of the second valve system 20.

Compressed air is fed from the compressor 10 by a feed line 26 to the structural unit of FIG. 2 while the compressor is in operation. The compressed air is relatively hot as a result of the compression and reaches temperatures of up to about 115° C. Since the cleaning and drying of the compressed air can be carried out only below temperatures of about 60° C, the compressed air must first of all be cooled to this temperature. This is done in a cooling coil 28 which wraps around the entire length of the adsorption filter 30 which is shown broken-off in the drawing. The cooling coil 28 is part of the cooling apparatus designated 12 in FIG. 1.

From the cooling unit 28, the cooled compressed air passes to the inlet opening 32 of the separator 34 which is formed as one unit with the valve system 14. The separator 34 comprises a cyclone-type oil and water separator in which condensation products are removed from the compressed air which is supersaturated after the cooling in the cooling coil 28. The condensation products are collected in a collecting chamber 36 at the lower end of the precipitator or oil and water separator 34 below a baffle plate 38.

The oil and water separator 34 is contained in a chamber which is closed at the top by a flexible diaphragm 40. To the bottom side of the diaphragm 40 facing the chamber there is fastened a valve tappet 42 which cooperates with a valve seat 46 at the bottom of the collecting chamber 36. The valve tappet 42 and valve seat 46 together form the closable branch opening or tap 16 of the apparatus of FIG. 1.

At the upper end of the chamber which contains the oil and water separator 34 but below the diaphragm 40 there is provided an outlet duct 48 which extends through a filter screen 50 to various individual valves of the valve means 14. As illustrated in FIG. 2, a total of four individual valves 52 to 55 are provided, the operation of which will be explained below.

The individual valves include, first of all, a suction ejector device which is referred to below in usual manner as a Borda nozzle 52. The nozzle opening of the Borda nozzle 52 is surrounded by a chamber 55' which is in communication by a connecting line 56 with a hollow space 58 above the diaphragm 40. When compressed air flows into the separator 34 through the inlet opening 32 and through the line 48 to the Borda nozzle 52, a vacuum is produced in the chamber 55' and acts through the connecting line 56 on the hollow space 58 above the diaphragm 40, thus lifting the diaphragm and thereby pulling the valve tappet 42 against the valve seat 46 to close the tap opening. The compressed air supplied by the compressor 10 to the separator 34 can therefore not escape through the tap opening 16.

Parallel to the Borda nozzle 52 there is provided, as second individual valve, a spring loaded bypass valve 53 which opens when a pressure gradient of about 0.1 bar is reached and maintains an approximately constant pressure drop across the Borda nozzle 52. Hence only a slight pressure drop is present even in the case of large quantities of flow, so that even with full of compressed air by the compressor the Borda nozzle 52 maintains a pressure difference of about 1 bar between the top of the diaphragm 40 and the bottom thereof. The other individual valves 54 and 55, which will be described below, remain normally closed during the feeding of compressed air to the compressed air storage tank 22 by the compressor 10. Downstream of the individual valves 52 to 55 is the outlet opening 60 of the valve system 14.

From the outlet opening 60 the prepurified saturated compressed air passes to the filter 18 which comprises an additional filter screen 62 and an adsorption filter 30. At the upper end of the adsorption filter 30, the dried compressed air passes through a sintered filter 64 as well as an after filter 66. Finally, the air passes from the filter 18 by a line 68, in which a nonreturn valve 69 is provided, to the compressed air tank 22. The nonreturn valve 69 is a part of the second valve system 20 in FIG. 1. The air tank 22 is provided with a valve controlled line 22a leading to the point of use of the compressed air.

Figure 3:
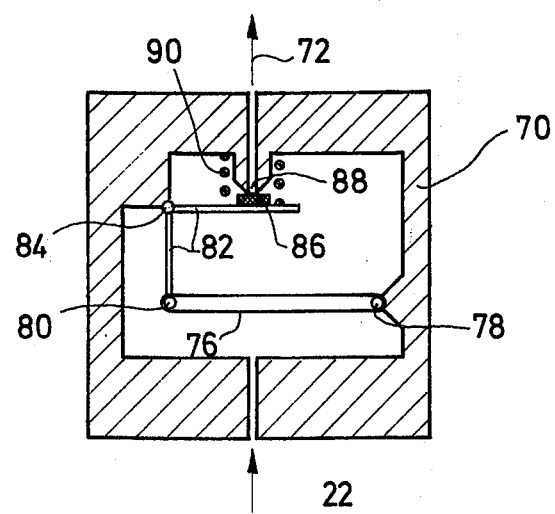
FIG. 3 is a schematic section of a valve for the apparatus in accordance with FIG. 1 which can be actuated by means of a moisture-sensitive feeler element.

Connected to the compressed air storage tank 22 is a valve 70 which is shown in FIG. 3 and which is a part of the second valve system 20. The outlet of the valve 70 is connected by a return line 72 with the filter 18, and specifically with a filter head 74 thereof which will be described in further detail below.

The valve 70 contains an actuating element a resin band 76, for instance of a suitable polyamide, which stretches upon an increase in the moisture content of the copressed air storage in the compressed air storage tank 22. The resin band 76 has its one end 78 connected firmly to the valve housing of the valve 70 and has its other end 80 connected to the lower end of a bell crank lever 82 which is swingable around a pivot point 84. The upper arm of the bell crank lever 82 which extends horizontally in the drawing is formed as a plate which faces away from the resin band 76 and bears a seal, for instance in the form of a small pad of rubber 86, by which a valve opening 88 can be closed. The arm of the bell crank lever 82 which bears the rubber pad 86 is acted on by the pressure within the compressed air tank 22 in a direction to close the valve. In order to counteract these pressure forces, a compressor spring 90 acts downwardly on the plate-shaped arm. The resin band 76, the length of the lever arms, the area of the lever arm bearing the rubber pad 86 and the compression spring 90 are so dimensioned that the rubber pad 86 releases the valve opening 88 when the compressed air in the compressed air tank 22 reaches a predetermined moisture content so that a regenerating cycle can be initiated as soon as the compressor 10 is disconnected and the tap opening 16 opened.

Upon the disconnecting of the compressor 10, an equalization of pressure first of all takes place between the top and the bottom of the diaphragm 40 since the Borda nozzle 52 can no longer maintain a vacuum in the hollow space 58 as a result of the absence of flow through the valve. After pressure equalization has been effected, the valve tappet 42 drops away from the valve seat 46 so that the tap opening 16 is now opened. The oil-water mixture which has collected during the charging process first of all flows outward through the opening 16 behind which a muffler is preferably provided. Thereupon the compressed air which has remained in the filter 18 flows out through the third individual valve of the valve system 14 which comprises a check valve 54. The check valve 54 is shown as comprising a diaphragm or valve plate 54a which is movable between a closed position in which it seats on an annular valve seat as shown in the drawing and an open position in which it is unseated. The valve blocks flow in a direction from the separator 34 to the filter 18 while permitting flow from the filter 18 to the separator 34 and thence out through the tap opening 16 when the latter is open.

Upon the disconnecting of the compressor or the feeding of compressed air from a supply system, different conditions prevail in the filter 18 and the valve system 14 depending upon the position of the valve 70. If the valve 70 is closed at the time of the disconnecting of the compressor 10, i.e., if the compressed air in the compressed air storage tank 22 is still so dry that no regenerating of the adsorption filter 30 of the filter 18 is necessary, the pressure in the filter 18 as well as in the valve system 14 will drop to atmospheric pressure and the system then remains at rest until the pressure in the compressed air tank 22 falls below a lower limit, whereupon the compressor 10 is again started by the pressure responsive switch 24. As soon as air again flows from the compressor into the oil-water separator 34, the diaphragm 40 will suddenly be lifted and the tap opening 16 closed so that the compressed air, after passing through the filter 18, is finally pumped through line 68 to the compressed air storage tank 22.

On the other hand if the valve 70 is open when the compressor is disconnected, then after the equalization of pressure on opposite sides of the diaphragm 40, and the opening of the tap opening 16, dry compressed air will flow out of the compressed air storage tank 22 through the adsorption filter 30, which is thereby regenerated and out through the tap opening 16. In this connection, the pressure in the adsorption filter 30 and in the valve system 14 drop approximately to atmospheric pressure. The pressure which is established depends on the flow conditions and resistances in the valve system 14. The regenerating cycle terminates as soon as the compressor starts up again.

If the compressor 10 interrupts its operation only for a very short period of time, for instance for less than five seconds, as may be the case in event of brief interruptions of current in the feed circuit of an electric motor driving the compressor, there is the danger that the pressure in the valve system 14 and in the filter 18 has not yet dropped to atmospheric pressure when the compressor is restarted. In such case, the compressed air supplied by the compressor 10 is not able to lift the diaphragm 40 so that, unless special measures are taken, with the tap opening 16 open there would gradually be established an equilibrium condition in which practically the entire air delivered by the compressor 10 would escape through the tap opening 16. In order to prevent this, a fourth individual valve is provided in the valve system 14 in the form of a cut-off valve 55 which is actuatable pneumatically against the pressure of a reset spring. The cut-off valve, as illustrated in the drawing, comprises a piston 96 working in a chamber 55a which is connected at its top by a connecting line 92 with the outlet opening 60 of the valve system 14 and is thus acted on by the pressure in the filter 18. A compressing spring 94 acts against the bottom of the piston. As soon as the pressure on the top of the piston drops below a given lower limit the spring 94 forces the piston 96 upward so that a skirt portion 96a opens a connection between line 56 connected with the hollow space 58 on the top of the diaphragm 40 and a throttle valve 98 which opens into the atmosphere. In this way the result is obtained that when the compressor 10 starts again after it has been interrupted for only a short time, the required pressure difference is very rapidly produced between the two sides of the diaphragm 40 so that the tap opening 16 is definitely closed after a short starting up phase, whereupon the delivery of compressed air to the compressed air storage tank 22 can again take place. On the other hand, the cut-off valve 55 in no way prevents the return of compressed air from the tank 22 through the adsorption filter 30 since during rthe regenerating phase only small quantities of air flow at low pressure through the valve system so that an equalization of pressure is always assured between the two sides of the diaphragm 40. It has also been found desirable if the auxiliary valve 55 instead of containing a piston has a diaphragm provided with a valve member which at sufficiently high pressure at the outlet opening 60 of the valve system 14 closes a valve opening which leads to the throttle valve 98 and opens this valve opening as soon as the valve member is lifted off from the valve opening by a compression spring at the pressure drops.

As already mentioned above, a special filter head 74 is provided at the upper end of the adsorption filter 30. The filter head 74 has within it a hollow space 74a containing the after filter 66 below which the sintered filter 64 is arranged. The feed line 26 through which the hot compressed air flows from the compressor 10 passes through the filter head 74 without, however, being connected to the space 74a. This construction has the advantage that the filter head 74 is heated up when the compressor 10 is in operation so that the compressed air arriving through the return line 72 is heated during the regenerating phases and thus has an improved drying effect. From the above it is clear that FIG. 2 is only very schematic with respect to the arrangement of the lines 26 and 72 and the filter head 74 and that in actual practice said lines are laid in such a manner as to assure optimum heating of the filter head 74 and optimum transfer of heat to the return line 72.

Another advantage of the construction of the invention is that all parts of the valve system 14 are arranged in a single block which consists preferably of a naterial of good thermoconductivity, for instance aluminum, so that practically no temperature gradient results between the inlet opening 32 and the outlet oening 60. This is important insofar as adsorption filters are very sensitive to supersaturated compressed air. By this construction of the filter system and valve system the result is obtained that practically no further cooling of the compressed air takes place beyond the oil-water separator 34 so that saturated and not supersaturated compressed air is fed to the adsorption filter 30 which, furthermore, is connected directly with the housing block of the valve system 14. The compact construction of the filter 18 and of the valve system 14 in the form of a single structural unit thus leads to relief of the adsorption filter 30 and to shortened times of regeneration and on the whole to a longer life expectancy of the adsorption filter. Furthermore, the construction of the valve system 14 has the advantage that with the pneumatic pressure present or pressures derived therefrom all vlve functions can be controlled so that additional control devices and particularly electrical control devices can be dispensed with. The dispensing with additional electric control devices in particular is very advantageous since the device can now be shipped to all countries completely mounted without regard to the different national and international regulations with regard to electrical safety and regardless of the different power line voltages and frequencies. It is merely necessary at the place of installation to provide a suitable compressor or a suitable drive motor for the compressor or some other source of compressed air.

Finally, it may also be pointed out that it is favorable to provide in the return devices a throttle valve by means of which the air returned into the adsorption filter can be substantially reduced in pressure so as to obtain an optimum utilization of the regenerating air and thus a high efficiency. In the embodiment in question the valve opening 88 has the effect of a throttle valve, it being so narrow, having for instance a diameter of only 0.75 mm, that the pressure in the adsorption filter 30 during the regenerating phases only slightly exceeds atmospheric pressure.

Furthermore, in devices with and particularly without a compressor, it is advantageous to provide a connection for a compressed air supply directly at the inlet opening 32 since when compressed air is fed from a compressed air network the compressed air need not be cooled.

FIGS. 4 to 7 show an embodiment which is similar except for two parts to the one shown in FIG. 2. Identical parts are identified by the same reference numbers. With respect to these parts and their matter of operation reference is had to the explanation given of the preceding examples.

Figure 4:
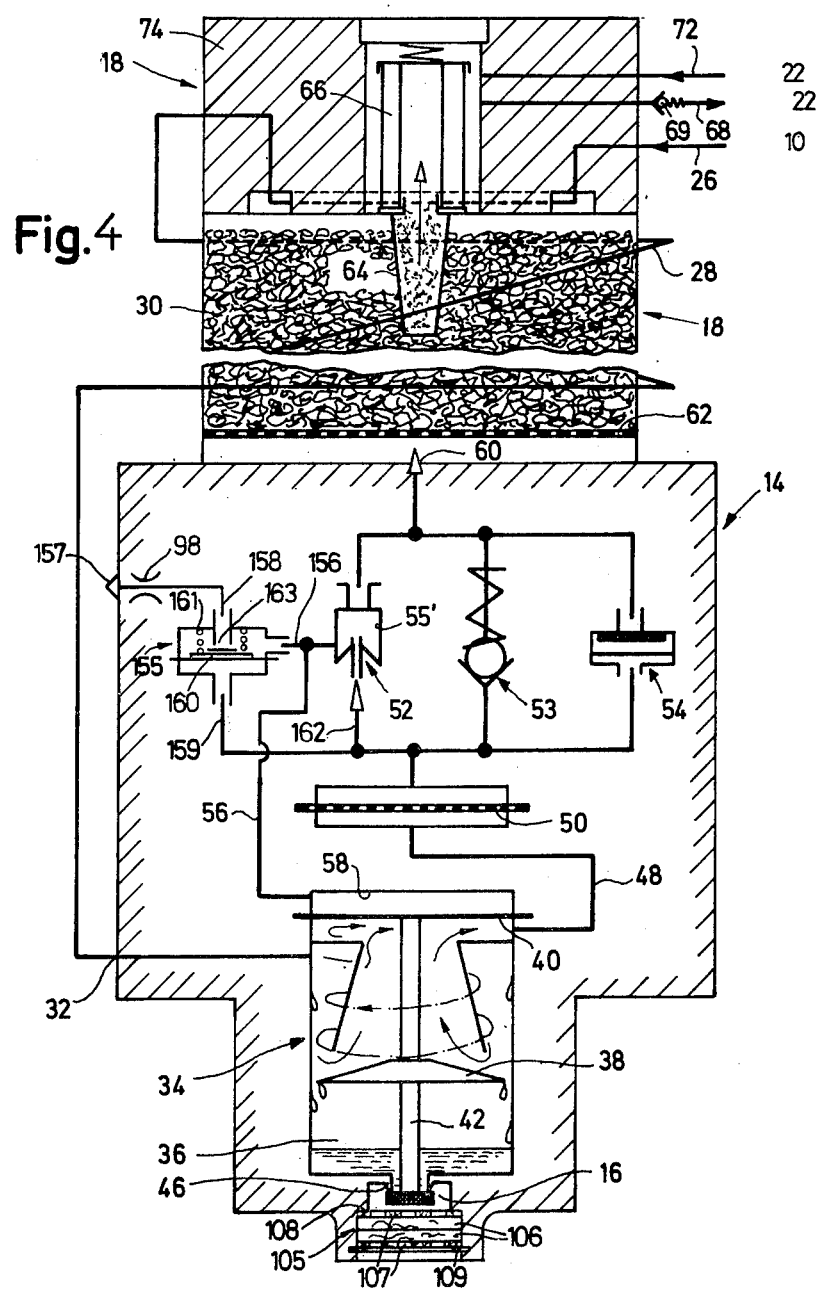
FIG. 4 is a schematic view corresponding to FIG. 2 showing another embodiment of the valve system.
Figure 5:
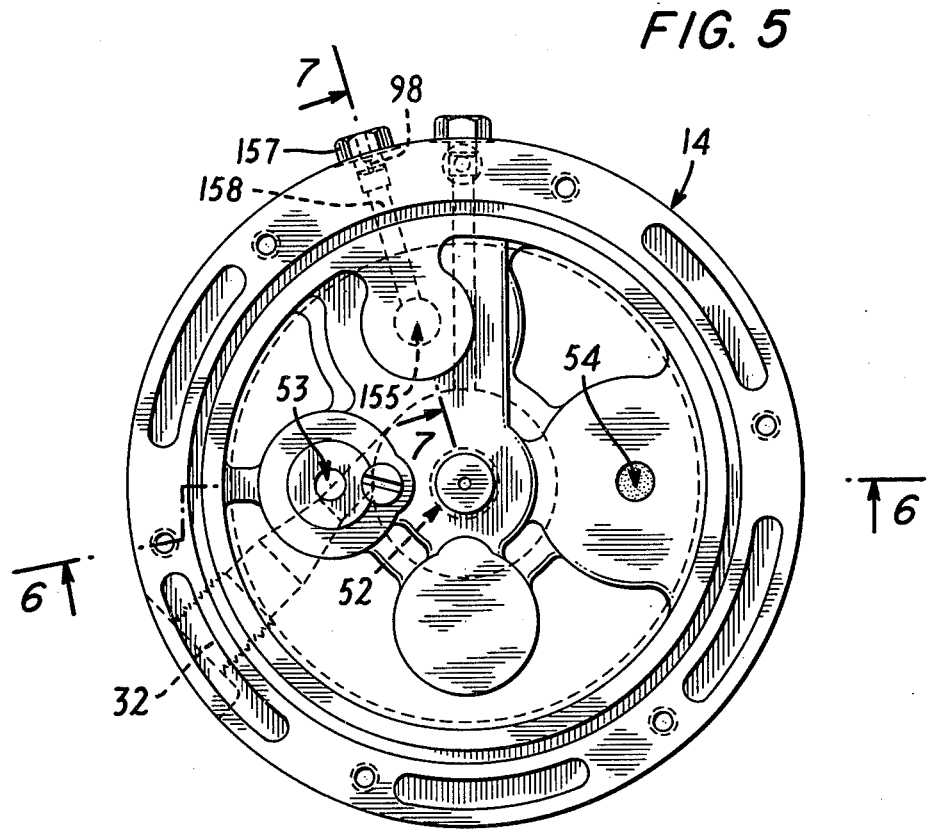
FIG. 5 is a plan of a valve assembly and separator such as is shown in FIG. 4.
Figure 7:
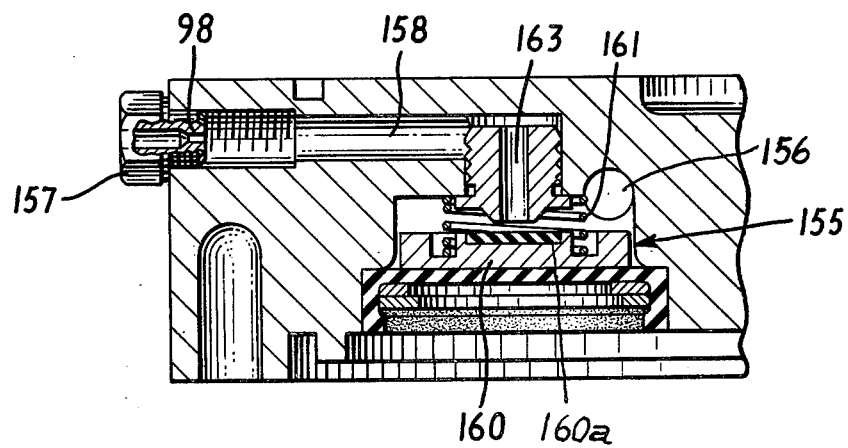
FIG. 7 is a section taken on line 7—7 in FIG. 5 and showing a fourth valve.
Figure 6:
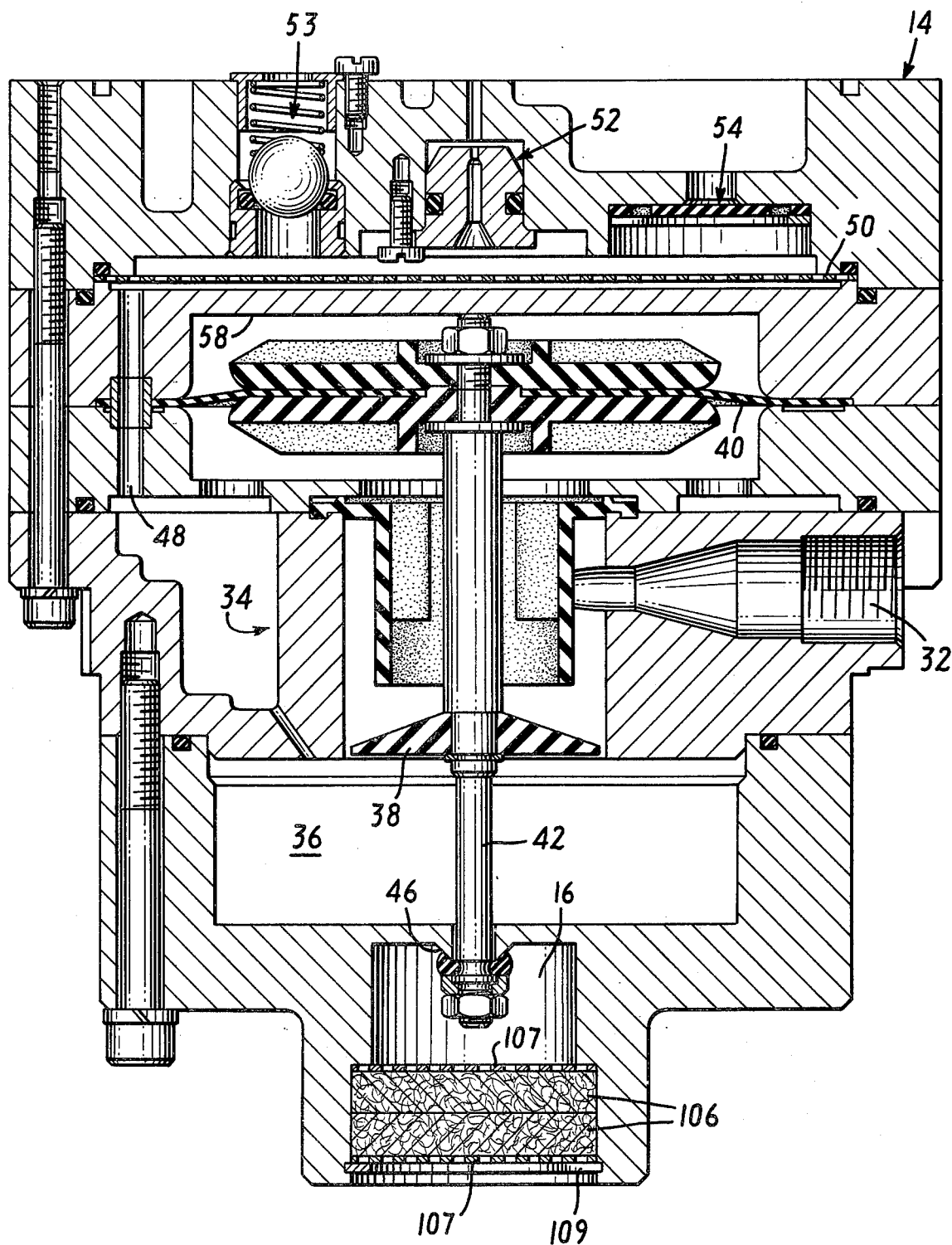
FIG. 6 is a section taken on line 6—6 in FIG. 5.

On the one hand there is shown in FIG. 4 a noise-silencing filter 105 for the tap opening 16. It consists of two thick felt disks 106 which are arranged between perforated supporting disks 107 the upper of which rests against a collar 108 and the lower of which is held fast by means of a lock washer 109.

On the other hand, the auxiliary valve 155 corresponding to the auxiliary or cut-off valve 55 in FIG. 2 is developed slightly differently. The auxiliary valve 155 also serves for the opening and closing of a line 156, 158 between the chamber 55' of the Borda nozzle 52 and the point of emergence to the atmosphere indicated by the arrow 157. A throttle 98 is also present in the line 158. The auxiliary valve 155 can assume two positions, namely "open" and "closed". A closure member 160 is acted on, on opposite sides, by pressure from the lines 156 and 159 respectively, a compressing spring 161 being provided in addition on the side on which the pressure from the line 156 acts so that the auxiliary valve 155 operates under the action of an air pressure and the force of the spring 161. A line 159 is connected with the inlet line 162 of the Borda nozzle 52 while the line 156 is connected with the line 56 leading to the chamber 58 and furthermore with the chamber 55'. The closure member 160 consists of a diaphragm clamped tightly in the housing and bearing a pressure and sealing plate 160a which can close the outlet opening 163 connected with line 158 and against which there rests the weak compression spring 161, the other end of which rests against the housing wall. As the result of the fact that the closure member 160 rests against a seat surrounding the outlet opening 163, the effective area subject to pressure on the top of the closure member 160 is less than on the bottom thereof. In this connection the effective surface areas on opposite sides of the closure member 160 and the force of the spring 161 are so adapted to each other that when a flow takes places in the Borda nozzle 52 in the direction indicated by arrow in line 162 and therefore a lower pressure is present in the chamber 55' than in the line 162, the connection of the line 156, 158 is closed off, while when there is no flow through the Borda nozzle in the direction of the arrow shown in the line 162 and therefore no pressure drop takes place in the chamber 55' because, for instance, the system is at rest or a slight flow takes place in the opposite direction, and accordingly the same pressure prevails on both sides of the closure member 160 of the auxiliary valve 155 and the lines 156 and 159, the auxiliary valve 155 is then open by the force of the spring 161 when the pressure in the lines connected with the auxiliary valve 155 lies below a predetermined minimum pressure.

The auxiliary valve 145 serves the same purpose as the auxiliary valve 55 of the first embodiment and operates in principle in the same manner. However, it can adjust itself better—and with more reliability—to different operating conditions which occur. If, for example, the feed of compressed air to the inlet opening 32 of the valve system 14 is disconnected only for a short time, for example when the compressor stops as a result of a brief interruption of current, a residual pressure remains in the filter 18 and the valve system 14, as a result of the resistances to flow in the lines and valves and the merely brief period of time, which is not sufficient for a complete equalization of pressure. This residual pressure will be approximately the same as the outlet oening 60 and in the line 162, particularly as the check valve 54 makes free backward flow possible. Since no flow takes place in the Borda nozzle 52 which would cause a decrease in pressure in the chamber 55', the same pressure prevails on both sides of the closure member 160 of the auxiliary valve 155. When this pressure drops below a pressure of, for instance, 3.5 bar, the spring 161 opens the connection of the line 156, 158 so that atmospheric pressure is established in this line, the line 56 and the chamber 58 while a certain residual pressure still prevails in the rest of the system. If the feed of compressed air again starts at the inlet opening 32, the diaphragm 40 can suddenly rise up and close the tap opening 16 so that the compressed air fed does not escape through the tap opening 16 but flows in the direction toward the filter 18 and thus also through the line 162 and the Borda nozzle 52 so that there is again produced in the chamber 55' a vacuum which acts on the top of the closure member 160 of the auxiliary valve 155 and here immediately closes the opening 163 against the weak spring 161 thereby making the transmission of the vacuum from the chamber 55' to the chamber 58 above the diaphragm 40 possible. During the opening and particularly in intermediate positions of the closure member 160, the throttle 98 prevents excessively rapid flow of air through the auxiliary valve 155. By its construction as a diaphragm valve, the auxiliary valve 155 operates practically without friction which is very important since the valve system is intended predominantly for air which does not contain oil and accordingly lubrication of pistons or the like is to be avoided.

The valve system of both embodiments shown can also be used individually wherever purely pneumatic control is desired for the connecting and disconnecting of the feeding of compressed air. The pneumatic valve system can also be used to relieve the line from the compressor to the storage tank without a drier and separator or also merely with an oil-water separator without an adsorption filter.

What I claim and desire to secure by letters patent is:

1. Apparatus for producing dry compressed air comprising a dry compressed air storage container, means for delivering dry compressed air from said storage container to a point of use, a source of compressed air for supplying compressed air to said storage container, flow connection means connecting said source to said storage container to supply compressed air from said source to said storage container, filter means including an adsorption filter disposed in said connection means between said source and said storage container for filtering and drying the compressed air supplied from said source to said storage container, means responsive to pressure in said storage container for discontinuing the supply of compressed air from said source to said storage container when the pressure in said storage container reaches a predetermined value, a valved controlled discharge outlet in said flow connection means between said adsorption filter and said source, and control means for effecting reverse flow of air from said storage container back through said adsorption filter and said discharge outlet to the atmosphere when the supply of compressed air from said source is discontinued to regenerate said adsorption filter, said control means comprising valve means responsive to the moisture content of compressed air in said storage container to effect said reverse flow only when the moisture content of said air is also a predetermined value.

2. Apparatus according to claim 1, in which said control valve means comprises a movable valve member for controlling reverse flow of air through said adsorption filter, a moisture sensitive element a dimension of which changes with change of moisture content of the air to which said element is exposed, said moisture sensitive element being exposed to the air of said storage container, and means physically connecting said element with said valve member for actuation of said valve member by change of dimension of said element.

3. Apparatus according to claim 2, in which said moisture sensitive element comprises a band of plastic material the length of which changes with changes in moisture.

4. Apparatus according to claim 3, in which said connecting means comprises a lever mechanism one arm of which is connected with said moisture sensitive element and one arm of which is connected with said valve member.

5. Apparatus according to claim 2, comprising spring means for biasing said valve member to a closed position.

6. Apparatus according to claim 1, in which said storage container comprises a single vessel for supplying dry compressed ar both for use and also for regeneration of said adsorption filter.

7. Apparatus according to claim 1, in which said valve means is connected between said storage container and said adsorption filter.

8. Apparatus according to claim 1, in which said adsorption filter has an exit portion comprising a filter head, and in which said compressed air source is a compressor and said flow connection means comprises a cooling coil which is connected in circuit between said compressor and said filter means and is in heat-exchanging relation with said filter head to heat said filter head and thereby supply heat to said reverse flow air for regenerating said adsorption filter.

9. Apparatus according to claim 1, in which said filter means further includes screen means connected in series with said adsorption filter.

10. Apparatus according to claim 9, in which said filter means further comprises a sintered filter between said adsorption filter and said storage container.

11. Apparatus according to claim 1, comprising separator means connected in circuit between said compressed air source and said filter means, said separator comprising means for removing condensates from the compressed air, a receptacle for collecting said condensates and a valved tap opening for discharging collected condensates, said valved top opening defining said discharge outlet, and pneumatically operated means controlling the opening of said tap opening.

12. Apparatus according to claim 11, in which said pneumatically operated means comprises a diaphragm for controlling said valved tap opening, a suction ejection nozzle (Borda nozzle) connected in circuit between said separator and said filter means for creating a pressure differential when air flows through said nozzle, and means for applying said pressure differential to opposite sides of said diaphragm to close said tap opening.

13. Apparatus according to claim 12, in which said pneumatically operated means includes a spring loaded bypass valve connected in parallel with said nozzle.

14. Apparatus according to claim 12, in which said pneumatically operated means includes a check valve connected in parallel with said nozzle and oriented to permit reverse flow of compressed air through said filter means.

15. Apparatus according to claim 12, in which said pneumatically operated means includes pressure responsive cut-off valve means for applying atmospheric pressure to one side of said diaphragm when air is supplied from said source but there is insufficient airflow through said nozzle to produce a sufficient pressure differential to close said tap opening.

16. Apparatus according to claim 11, in which said separator and pneumatically operated means are housed in a unitary housing block of thermoconductive material to maintain substantially uniform temperature throughout.

17. Apparatus according to claim 16, comprising a casing in which said adsorption filter is housed, said casing being adjacent and in heat-exchanging relation with said housing block to avoid any substantial temperature drop between said separator and said adsorption filter.

18. Apparatus a-cording to claim 1, in which said valve means comprises a restricted orifice to reduce the pressure of air returned from said storage container to said adsorption filter during said reverse flow approximately to atmospheric pressure.

19. Apparatus according to claim 18, in which said valve means comprises a valve having a restricted opening with a valve seat surrounding said opening, a valve member seatable on said seat, spring means biasing said valve member toward said seat and a moisture sensitive element connected with said valve member for moving said valve member from said seat when the moisture content of compressed air of said storge tank exceeds a predetermined value.

20. Apparatus according to claim 1, in which a valve housing mounted on said compressed air storage container has an inner space which is connected with the interior of said container, said moisture responsive valve means being disposed in said space and comprising a movable valve member, a moisture sensitive element a dimension of which changes with the moisture content of air in said space and means connecting said element with said valve member for actuation of said valve member by change of dimension of said element.

* * * * *